United States Patent
Sala Cunill et al.

(10) Patent No.: US 10,431,068 B2
(45) Date of Patent: Oct. 1, 2019

(54) CONTROLLING PRODUCTS CONTAINED IN CONTAINER DEVICES

(71) Applicant: ADAN MEDICAL INNOVATION, S.L., Barcelona (ES)

(72) Inventors: Anna Sala Cunill, Les Botigues de Sitges (ES); Adrian Curran, Les Botigues de Sitges (ES); Santiago Pérez De La Hoz, Mataró (ES); Marc Torrent Poch, Palafrugell (ES)

(73) Assignee: ADAN MEDICAL INNOVATION, S.L., Barcelona (ES)

( * ) Notice: Subject to any disclaimer, the term of this patent is extended or adjusted under 35 U.S.C. 154(b) by 0 days.

(21) Appl. No.: 15/560,470

(22) PCT Filed: Mar. 23, 2016

(86) PCT No.: PCT/EP2016/056443
§ 371 (c)(1),
(2) Date: Sep. 21, 2017

(87) PCT Pub. No.: WO2016/151042
PCT Pub. Date: Sep. 29, 2016

(65) Prior Publication Data
US 2018/0061208 A1    Mar. 1, 2018

Related U.S. Application Data

(60) Provisional application No. 62/136,903, filed on Mar. 23, 2015.

(51) Int. Cl.
*G08B 21/18* (2006.01)
*A61M 5/20* (2006.01)
(Continued)

(52) U.S. Cl.
CPC ........... *G08B 21/182* (2013.01); *A61M 5/142* (2013.01); *A61M 5/145* (2013.01); *A61M 5/20* (2013.01);
(Continued)

(58) Field of Classification Search
None
See application file for complete search history.

(56) References Cited

U.S. PATENT DOCUMENTS 10,086,138 B1 * 10/2018 Novak, Jr. .......... A61M 5/1723
10,293,120 B2 * 5/2019 Cabiri ................. A61M 5/5086
(Continued)

FOREIGN PATENT DOCUMENTS

WO    WO 2012/040528 A1    3/2012

OTHER PUBLICATIONS

International Search Report and Written Opinion of the International Searching Authority dated Aug. 17, 2016 for PCT/EP2016/056443, 19 pages.

*Primary Examiner* — Chico A Foxx
(74) *Attorney, Agent, or Firm* — Squire Patton Boggs (US) LLP (57) ABSTRACT

The disclosure relates to method of controlling a product contained in a container device, the method comprising, when the container device is arranged in a housing (101), receiving at least one signal from a sensor module (104), said signal representing an attribute related to the product contained in the container device, said sensor module being associated with the housing; determining if the attribute represented by the signal received from the sensor module is a warning attribute; if the attribute is a warning attribute, generating at least one trigger signal to be received by at least a warning module configured to generate a warning based on the trigger signal.

17 Claims, 3 Drawing Sheets

(51) Int. Cl.
*A61M 5/142* (2006.01)
*A61M 5/145* (2006.01)

(52) U.S. Cl.
CPC ..... *A61M 2205/17* (2013.01); *A61M 2205/18* (2013.01); *A61M 2205/33* (2013.01); *A61M 2205/3306* (2013.01); *A61M 2205/3313* (2013.01); *A61M 2205/3368* (2013.01); *A61M 2205/35* (2013.01); *A61M 2205/3576* (2013.01); *A61M 2205/50* (2013.01); *A61M 2205/70* (2013.01)

(56) References Cited

U.S. PATENT DOCUMENTS

| | | | |
|---|---|---|---|
| 2002/0040208 A1 | 4/2002 | Flaherty et al. | |
| 2003/0216683 A1 | 11/2003 | Shekalim | |
| 2006/0241552 A1* | 10/2006 | Tang | A61M 5/1684 604/253 |
| 2008/0184719 A1* | 8/2008 | Lowenstein | F25D 29/00 62/127 |
| 2009/0002185 A1* | 1/2009 | Chu | G06K 17/0022 340/666 |
| 2011/0227734 A1* | 9/2011 | Ortenzi | G08B 13/1436 340/568.1 |
| 2012/0184907 A1 | 7/2012 | Smith et al. | |
| 2014/0207080 A1* | 7/2014 | Allerdings | A61M 5/31525 604/207 |
| 2016/0206806 A1* | 7/2016 | Wright | A61M 5/002 |

\* cited by examiner

CONTROLLING PRODUCTS CONTAINED IN CONTAINER DEVICES

This application claims the benefit of U.S. Provisional Patent Application Ser. No. 62/136,903 filed on the 23 of Mar. 2015.

FIELD OF THE INVENTION

The present disclosure relates to the control of products contained in container devices and more specifically to methods, systems and computer program products for controlling a product contained in a container device.

BACKGROUND ART

Allergies are very common worldwide and their prevalence is increasing. An allergic reaction is a hypersensitivity disorder of the immune system. The immune system normally protects the body from harmful agents such as bacteria and toxins. Its overreaction to an otherwise harmless substance is called an allergic reaction. The substance that causes a reaction is called allergen.

The severity of the reaction depends on the person's immune system response, and it could range from mild to severe.

For example, anaphylaxis is an acute multisystemic severe allergic reaction that is rapid on onset and may cause death. In fact, a fatal event has been reported to occur in 0.5-2% of cases of anaphylaxis. The most frequent triggers are food and drugs, followed by stings, latex, anisakis and other causes.

The only adequate treatment during an anaphylaxis is applying as soon as possible an injection of epinephrine (also known as adrenaline). Thus, patients who have anaphylactic reactions must carry auto-injectable doses of epinephrine always with them, as recommended in all the medical guidelines. The auto-injector or injector pen of epinephrine will allow them to apply the doses to themselves in case of anaphylaxis.

However, in practice this has many drawbacks:
  The patient has to control the epinephrine, performing a periodic visual inspection (evaluating transparency) and controlling temperature, as the effectiveness of the epinephrine depends on the active ingredient being in good condition;
  The patient might forget to carry the auto-injector or even deliberately not carry it because they might be ashamed and see it as a stigma as it discloses they have an illness;
  The patient might be afraid of injecting the epinephrine, due to unfamiliarity with its use or fear of adverse events. In more serious reactions it could happen that the patient cannot self-inject the drug because he/she is unconscious;
  The patient might forget or might not know how to use the auto-injector or injector pen.

Consequently, there is a need for a system that at least partially solves the aforementioned problems.

SUMMARY OF THE INVENTION

In a first aspect, a method of controlling a product contained in a container device is disclosed. The method may comprise, when the container device is arranged in a housing:
  Receiving at least one signal from a sensor module, said signal representing an attribute related to the product contained in the container device, said sensor module being associated with the housing;
  Determining if the attribute represented by the signal received from the sensor module is a warning attribute;
  If the attribute is a warning attribute, generating at least one trigger signal to be received by at least a warning module configured to generate a warning based on the trigger signal.

This way, it is possible to detect if the product contained in the container device is in a suitable status to be used or about to be used. The provision of the step of receiving at least one signal from the sensor module allows monitoring different attributes related to the product. Attributes related to the product may be attributes directly related to the product or indirectly related to the product. Attributes directly related to the product may be, for example, characteristics of the product such as physicochemical characteristics or temperature. Attributes indirectly related to the product may be, for example, the opening of the housing or the emergence of the container device from the housing, which may involve the extraction of the product from the housing and consequently the use of the product due to, for example, health problems of the user. Another indirect attribute could be the temperature in the vicinity of the container device inside the housing or the temperature of the container device, which may cause the spoilage of the product.

On the other hand, the provision of the step of determining if the attribute represented by the signal received from the sensor module is a warning attribute allows knowing if any of the attributes sensed by the sensor module may be relevant for the status of the product or if the product is about to be used.

The step of generating at least one trigger signal to be received by at least a warning module allows providing to the user or to any other person nearby or to any person related to the user a warning about the product or its possible use.

The product contained in the container device may comprise, for example, at least one of the following elements (among other options): a drug; a degraded drug; a modified drug; a pharmaceutical or veterinary composition; a degraded pharmaceutical or veterinary composition; a modified pharmaceutical or veterinary composition; an excipient; a degraded excipient; a modified excipient; a formulation; an aggregate; a metabolite or by-product of any of the aforementioned.

This way, in case the product comprises a drug, the drug may be, for example, epinephrine.

With reference to the container device, it may be a drug delivery device, such as an injector pen.

In some examples, the received signal representing an attribute related to the product contained in the container device may comprise a signal representing a physicochemical characteristic of the product, and determining if the attribute represented by the signal received from the sensor module is a warning attribute may comprise determining if the physicochemical characteristic of the product contained in the container device is outside an established range.

The definition of said established range basically depends on the physicochemical characteristic, that is, each physicochemical characteristic may require a different range. A skilled person can determine every range taking into account, for example, the product and the physicochemical characteristic of the product to be controlled.

If the value of the physicochemical characteristic represented by the signal provided by the sensor module is inside the established range means that the physicochemical characteristic of the product is acceptable and consequently the status of the product may be suitable for use. On the contrary, if the value of the physicochemical characteristic represented by the signal provided by the sensor module is outside the established range means that the physicochemical characteristic of the product is not acceptable and consequently the status of the product may be not suitable for use or it may be in danger of becoming not suitable for use and a warning indicating this situation may be generated.

According to some examples, the physicochemical characteristic of the product contained in the container device may comprise at least one of the following physicochemical characteristics: Absorbance; Transmittance; Optical density; Transparency; Attenuation; Diffraction; Fluorescence; Refraction.

In some examples, the received signal representing an attribute related to the product contained in the container device may comprise a signal representing the temperature in the vicinity of the container device inside the housing, and determining if the attribute represented by the signal received from the sensor module is a warning attribute may comprise determining if the temperature in the vicinity of the container device inside the housing is outside an established range.

The definition of said established range basically depends on the product contained in the container device, that is, each product may require a different range. A skilled person can determine every range taking into account, for example, the product to be controlled. If the value of the temperature in the vicinity of the container device represented by the signal provided by the sensor module is inside the established range means that said temperature is acceptable and consequently the status of the product may be suitable for use. On the contrary, if the value of the temperature represented by the signal provided by the sensor module is outside the established range means that the value of temperature is not acceptable and consequently the status of the product may be not suitable for use or it may be in danger of becoming not suitable for use and a warning indicating this situation may be generated.

In some examples, the received signal representing an attribute related to the product contained in the container device may comprise a signal representing the temperature of the container device, and determining if the attribute represented by the signal received from the sensor module is a warning attribute may comprise determining if the temperature of the container device is outside an established range.

The definition of said established range basically depends on the product contained in the container device, that is, each product may require a different range. A skilled person can determine every range taking into account, for example, the product to be controlled. If the value of the temperature of the container device represented by the signal provided by the sensor module is inside the established range means that said temperature is acceptable and consequently the status of the product may be suitable for use. On the contrary, if the value of the temperature represented by the signal provided by the sensor module is outside the established range means that the value of temperature is not acceptable and consequently the status of the product may be not suitable for use or it may be in danger of becoming not suitable for use and a warning indicating this situation may be generated.

According to some examples, the received signal representing an attribute related to the product contained in the container device may comprise a signal representing the temperature of the product, and determining if the attribute represented by the signal received from the sensor module is a warning attribute may comprise determining if the temperature of the product is outside an established range.

The definition of said established range basically depends on the product contained in the container device, that is, each product may require a different range. A skilled person can determine every range taking into account, for example, the product to be controlled. If the value of the temperature of the product represented by the signal provided by the sensor module is inside the established range means that said temperature is acceptable and consequently the status of the product may be suitable for use. On the contrary, if the value of the temperature represented by the signal provided by the sensor module is outside the established range means that the value of temperature is not acceptable and consequently the status of the product may be not suitable for use or it may be in danger of becoming not suitable for use and a warning indicating this situation may be generated.

In some examples, the received signal representing an attribute related to the product contained in the container device may comprise a signal representing the opening of the housing, and determining if the attribute represented by the signal received from the sensor module is a warning attribute may comprise determining if the housing has been opened. Basically, if the opening of the housing is detected, a warning may be generated because the user may be, for example, in danger (e.g. the user may have an allergic reaction such as anaphylaxis). On the other hand, said opening of the housing may be due to a visual inspection of the product or a replacement of the container device, for example, because the product has expired. In these cases, a warning may also be generated.

In some examples, the received signal representing an attribute related to the product contained in the container device may comprise a signal representing the emergence of the container device from the housing, and determining if the attribute represented by the signal received from the sensor module is a warning attribute may comprise determining if the container device has emerged from the housing. Thus, if the emergence of the container device from the housing is detected, a warning may be generated because the user may be, for example, in danger (e.g. the user may have an allergic reaction such as anaphylaxis). On the other hand, said emergence of the container device from the housing may be due to a visual inspection of the product or a replacement of the container device, for example, because the product has expired. In these cases, a warning may also be generated.

At this point it is important to highlight that the term "emergence" means that the container device (and consequently the product) exits from the housing voluntarily (the container device is removed from the housing by the user) or involuntarily (the container emerges from the housing without a user intervention).

According to another aspect, a computer program is disclosed. The computer program may comprise program instructions for causing a control module (or any other computing system) to perform a method of controlling a product contained in a container device as described above. The computer program may be embodied on a storage medium (for example, a CD-ROM, a DVD, a USB drive, on a computer memory or on a read-only memory) or carried on a carrier signal (for example, on an electrical or optical carrier signal).

According to another aspect, a control module for controlling a product contained in a container device, when the container device is arranged in a housing, is disclosed. The control module may comprise means for receiving at least one signal from a sensor module, said signal representing an attribute related to the product contained in the container device, said sensor module being associated with the housing; means for determining if the attribute represented by the signal received from the sensor module is a warning attribute; means for generating, if the attribute is a warning attribute, at least one trigger signal to be received by at least a warning module configured to generate a warning based on the trigger signal.

According to yet another aspect, a control module is disclosed. The control module may comprise a memory and a processor, embodying instructions stored in the memory and executable by the processor, the instructions comprising functionality to execute a method of controlling a product contained in a container device as described above.

In another aspect, a system is disclosed. The system may comprise a housing configured to arrange at least one container device; at least one sensor module configured to generate at least one signal representing an attribute related to the product contained in the container device, the sensor module being associated with the housing; at least one control module as described above, the control module being associated with the housing; at least one warning module configured to generate a warning based on the trigger signal generated by the control module.

In some examples, the sensor module may comprise at least one sensor element for generating a signal representing a physicochemical characteristic of the product, said physicochemical characteristic comprising, for example, Absorbance, Transmittance, Optical density, Transparency, Attenuation, Diffraction, Fluorescence and/or Refraction.

Said at least one sensor element, for example, may comprise at least one transducer configured to generate a signal and at least one receiver configured to detect changes in the signal generated by the at least one transducer. The at least one transducer and the at least one receiver, for example, may be arranged next to each other or may be arranged opposite to each other. Said signal generated by the at least one transducer may be, for example, one of the following signals: an electromagnetic signal or a radiation beam of the electromagnetic spectrum.

According to some examples, the sensor module may further comprise:
- at least one sensor element for measuring the temperature in the vicinity of the container device inside the housing; and/or
- at least one sensor element for measuring the temperature of the container device; and/or
- at least one sensor element for measuring the temperature of the product; and/or
- at least one sensor element for detecting the opening of the housing; and/or
- at least one sensor element for detecting the emergence of the container device from the housing.

In some examples, the warning module may comprise at least one of the following warning elements:
- At least one warning element for generating an audible warning (e.g. a speaker, a buzzer, etc.);
- At least one warning element for generating a visual warning (e.g. a display screen (for example, LCD), a plurality of LEDs (Light Emitting Diode), etc.);
- At least one warning element for generating a haptic warning (e.g. a vibrator motor).

In some examples, the warning module may be associated with the housing, that is, the warning module, for example, may be within or inserted into the housing. The same may be applied to the sensor module and the warning module.

According to some examples, the system may further comprise a satellite positioning module. Said module may be used for obtaining the geo-position of the system and consequently determining the geo-position of the user in case the user may be in danger (for example, health problems). Furthermore, in case the user has forgotten the system (and consequently the injector pen), he/she will be able to locate it with the geo-positioning.

In some examples, the system may comprise a communication module for communications from the system to an apparatus (or any other computing or electronic device that may be controlled by a user of the system), for example a portable apparatus such as a smartphone, a tablet, a smartwatch or a notebook. Through said apparatus, the system may cause the generation of warnings to the user, to any other person nearby or to any person related to the user.

In other examples, the system may comprise a telephone module configured to generate external warnings to the user, any person nearby or any person related with the user. Said external warnings may be SMS, emails, Whatsapp or Telegram messages, etc. Furthermore, the telephone module may be configured to make a telephone call to at least one established telephone number (for example to a pre-defined contact or an emergency service).

According to another aspect, a method of generating warning signals in an apparatus, the apparatus comprising a control module, a communication module and a warning module, is disclosed. The method may comprise:
- The apparatus control module receiving at least one trigger signal from a control module of a system for controlling a product contained in a container device as described above, through a communication established between the apparatus communication module and the system communication module;
- The apparatus control module generating at least one warning signal according to the received trigger signal to be received by the apparatus warning module configured to generate a warning according to the warning signal.

This way, the apparatus is configured to receive a trigger signal from the control module of a system as described above (at this point it is important to remember that the trigger signal is generated by the control module of the system when a warning attribute related to the product is determined), process it and generate a warning according to the received trigger signal. Thus, a relevant attribute related to the product contained in the container device may be communicated to a user, to any other person nearby or to any person related to the user in a more direct and personal way. Furthermore, the relevant attributes such as the use of the product may also be communicated, for example, to emergency services.

At this point it is important to highlight that the apparatus may be a standalone device controlled by the user.

In some examples, the trigger signal received from the system control module may represent that a physicochemical characteristic (such as transparency) of the product contained in the container device is outside an established range, and generating a warning signal may comprise generating a warning signal from which the warning module generates a warning about the physicochemical characteristic being outside the established range.

In some examples, the trigger signal received from the system control module may represent that the temperature in the vicinity of the container device inside the housing is outside an established range, and generating a warning signal may comprise generating a warning signal from which the warning module generates a warning about the temperature in the vicinity of the container device inside the housing being outside the established range.

According to some examples, the trigger signal received from the system control module may represent that the temperature of the container device is outside an established range, and generating a warning signal may comprise generating a warning signal from which the warning module generates a warning about the temperature of the container device being outside the established range.

In some examples, the trigger signal received from the system control module may represent that the temperature of the product is outside an established range, and generating a warning signal may comprise generating a warning signal from which the warning module generates a warning about the temperature of the product being outside the established range.

In some examples, the trigger signal received from the system control module may represent the opening of the housing, and generating a warning signal may comprise generating a warning signal from which the warning module generates a warning asking the reason for the opening of the housing.

According to some examples, the trigger signal received from the system control module may represent the emergence of the container device from the housing, and generating a warning signal may comprise generating a warning signal from which the warning module generates a warning asking the reason for the emergence of the container device from the housing.

In some examples, the method may further comprise waiting for receiving a response to the warning within an established time period.

If a response is not received (it may mean that the user may be in danger, for example, with a health problem), the method may comprise generating an external warning, that is, a warning, for example, to any person related to the user and/or an emergency service. If the apparatus comprises a satellite positioning module, the method may comprise obtaining the geo-position of the apparatus from the apparatus satellite positioning module and the external warning may comprise the geo-position of the apparatus, which may correspond to the geo-position of the user.

In some examples, generating an external warning may comprise making a telephone call to at least one established telephone number through a telephone module that may be comprised in the apparatus. Further or alternatively, generating an external warning may comprise sending an electronic message (for example, an SMS, an email, a Whatsapp or Telegram message, etc.), for example, to any person related to the user so that said person may know that the user may be in danger.

On the contrary, if a response is received, the method may further comprise:

The apparatus control module determining a reason from the received response;

If the reason relates to a replacement of the container device, the apparatus control module generating a warning signal from which the warning module generates a warning comprising instructions about the replacement of the container device;

If the reason relates to the use of the container device, the apparatus control module generating a warning signal from which the warning module generates a warning comprising instructions about the use of the container device.

If the reason relates to the use of the container device, the method may comprise generating an external warning. If the apparatus comprises a satellite positioning module, the method may further comprise obtaining the geo-position of the apparatus from the apparatus satellite positioning module and the external warning may comprise the geo-position of the apparatus, which may correspond to the geo-position of the user.

In some examples, generating said external warning may comprise making a telephone call to at least one established telephone number through a telephone module that may be comprised in the apparatus. Further or alternatively, generating an external warning may comprise sending an electronic message (for example, an SMS, an email, a Whatsapp or Telegram message, etc.), for example, to any person related to the user so that said person may know that the user may be in danger.

In some examples, the method may comprise:

The apparatus control module determining if a communication is established between the apparatus communication module and the system communication module;

In case the communication is not established, the apparatus control module generating a warning signal from which the warning module generates a warning about no communication established between the apparatus and the system.

This way, if the communication is not established, the control module of the apparatus cannot receive trigger signals from the control module of the system and consequently it is not possible to communicate warning attributes related to the product. In the same way, it is also not possible to generate external warnings to the user, to any other person nearby, or to any person related to the user. Therefore, it may be important to ensure that the communication between the system and the apparatus is established.

On the other hand, if the communication is not established, the control module of the apparatus may generate warning signals from which the warning module generates a warning about no communication established between the apparatus and the system. The communication may be not established because the apparatus and the system are very distant, for example, because the user leaves/forgets the system at home or loses the system, or due to a malfunction of the device or system.

According to another aspect, a computer program is disclosed. The computer program may comprise program instructions for causing a control module (or any other computing system) to perform a method of generating warning signals in an apparatus as described above. The computer program may be embodied on a storage medium (for example, a CD-ROM, a DVD, a USB drive, on a computer memory or on a read-only memory) or carried on a carrier signal (for example, on an electrical or optical carrier signal).

According to another aspect, a control module for generating warning signals in an apparatus, the apparatus comprising the control module, a communication module and a warning module, is disclosed. The control module may comprise means for receiving at least one trigger signal from a control module of a system for controlling a product contained in a container device as described above, through a communication established between the apparatus communication module and the system communication module;

means for generating at least one warning signal according to the received trigger signal to be received by the apparatus warning module configured to generate a warning according to the warning signal.

According to yet another aspect, a control module is disclosed. The control module may comprise a memory and a processor, embodying instructions stored in the memory and executable by the processor, the instructions comprising functionality to execute a method of generating warning signals in an apparatus as described above.

In another aspect, an apparatus is disclosed. The apparatus may comprise a communication module configured to establish a communication with a communication module of a system for controlling a product contained in a container device as described above; a control module as described above; a warning module configured to generate a warning based on the warning signal generated by the apparatus control module.

In some examples, the apparatus warning module may comprise at least one of the following warning elements:
  at least one warning element for generating an audible warning;
  at least one warning element for generating a visual warning;
  at least one warning element for generating a haptic warning.

In some examples, the apparatus may comprise a satellite positioning module. This way, it is possible to obtain the geo-position of the apparatus (and consequently the geo-position of the user).

According to some examples, the system may further comprise the apparatus as described above, wherein the system control module may comprise the apparatus control module and the system warning module may comprise the apparatus warning module.

At this point it is important to highlight that the apparatus may be a part of the system or may be provided remote with reference to the system. In the case where the apparatus is a part of the system, the control module of the system may be capable of executing its own method (that is, a method of controlling a product contained in a container device as described above) and a method of generating warning signals in an apparatus (that is, the method executed by the control module of the apparatus, which has been disclosed above). Furthermore, the warning module of the system may be capable of generating its own warnings as described above and the warnings generated by the warning module of the apparatus (for example, external warnings, etc.) as described above. Regarding the communication modules, the communication module of the system and the communication module of the apparatus may establish a communication of wired or wireless type or both communication modules may be the same module.

Alternatively, when the apparatus is a part of the system, it is also possible that the apparatus control module may execute a method of controlling a product contained in a container device as describe above (that is, the method executed by the system control module) and consequently it may be understood that the system control module may be comprised in the apparatus control module. The same may be applied to the warning modules, that is, the apparatus warning module may be capable of generating the warnings of the system warning module and consequently it may be understood that the system warning module may be comprised in the apparatus warning module.

On the other hand, the control module and/or the warning module of the system may be the control module and/or the warning module respectively of the apparatus. That is, the system does not comprise itself the control module and/or the warning module but it may use said modules comprised in the apparatus.

Additional objects, advantages and features of embodiments of the invention will become apparent to those skilled in the art upon examination of the description, or may be learned by practice of the invention.

BRIEF DESCRIPTION OF THE DRAWINGS

Particular embodiments of the present invention will be described in the following by way of non-limiting examples, with reference to the appended drawings, in which.

DETAILED DESCRIPTION OF EMBODIMENTS

Figure 1:
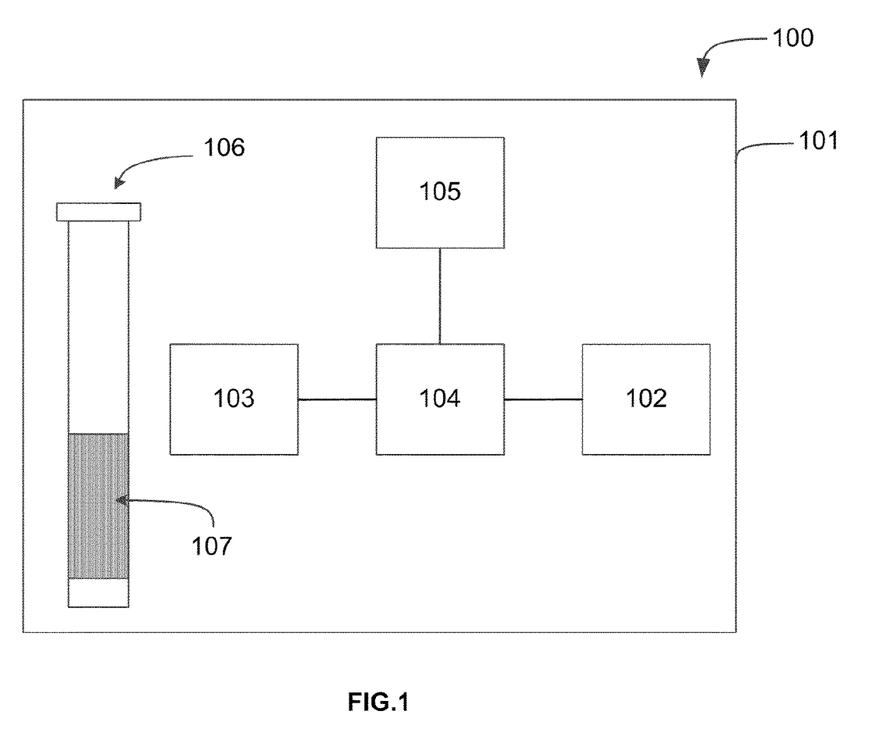
FIG. 1 illustrates a block diagram of a system for controlling a product contained in a container device according to some examples.

FIG. 1 illustrates a block diagram of a system for controlling a product contained in a container device.

The product may be in a liquid, gaseous or solid state and may comprise, for example, at least one of the following elements (or any combination of them):
  A drug;
  A degraded drug;
  A modified drug;
  A pharmaceutical composition;
  A degraded pharmaceutical composition;
  A modified pharmaceutical composition;
  An excipient;
  A degraded excipient;
  A modified excipient;
  A formulation;
  An aggregate;
  A metabolite or by-product of any of the aforementioned.

The term "drug" refers to a pharmaceutical active ingredient. Basically, a drug is a chemical compound that is active to treat a disease.

A "pharmaceutical composition" comprises a therapeutically effective amount of a pharmaceutically active ingredient together with one or more pharmaceutically acceptable excipients or carriers.

The expression "therapeutically effective amount" as used herein, refers to the amount of a compound that, when administered, is sufficient to prevent development of, or alleviate to some extent, one or more of the symptoms of the disease which is addressed.

The expression "pharmaceutically acceptable excipients or carriers" refers to pharmaceutically acceptable materials, compositions or vehicles. Each component must be pharmaceutically acceptable in the sense of being compatible with the other ingredients of the pharmaceutical composition. It must also be suitable for use in contact with the tissue or organ of humans and animals without excessive toxicity, irritation, allergic response, immunogenicity or other problems or complications commensurate with a reasonable benefit/risk ratio.

The term "formulation" refers to a combination of the drug with a variety of excipients or carriers to ensure a stable active medication following storage. The formulation type varies depending on the route of administration, and it can be topical, enteral or parenteral.

The term "aggregate" refers to several products grouped together or considered as a whole.

The term "metabolite" refers to intermediates and products of metabolism of a drug, formed as part of the natural biochemical process of degrading and eliminating the compounds. Metabolites can also have clinical effect.

The term "by-product" refers to secondary products derived from a chemical reaction.

On the other hand, the product may also comprise a veterinary composition that comprises a therapeutically effective amount of a veterinary active ingredient together with one or more veterinary acceptable excipients or carriers.

In the present examples, the product contained in the container device comprises a pharmaceutical composition comprising a therapeutically effective amount of epinephrine together with one or more pharmaceutically acceptable excipients or carriers. However, all that is described for this product may be applied to any other product.

With reference to the container device, it may be any device capable of containing any of the products described above or other products. Thus, for example, the container device may be a drug delivery device.

In the present examples, the container device is a drug delivery device such as an injector pen or an auto-injector, which contains the pharmaceutical composition described above. However, all that is described for this container device may be applied to any other type of container device, such as a portable container device.

The system may have different configurations. This way, the system may be, for example, a portable device or case (i.e. the user may carry the system) or may be a box or the like fixed in a surface (for example, in a restaurant or in a shopping center) or any other non-portable configuration.

Furthermore, the system may be configured to host one or more container devices.

In the present examples, the system is a portable case and it is configured to host only one injector pen. However, all that is described for this system may be applied to any other configuration of the system.

As can be seen in FIG. 1, a portable case 100 according to some examples comprises a housing 101, a power module 102 of the electronics, a sensor module 103, a control module 104 and a warning module 105.

More specifically, the housing 101 is configured to host or arrange an injector pen 106 containing the disclosed pharmaceutical composition 107. In the present examples, the housing comprises a cavity in which the injector pen is arranged. Obviously, the housing could have other solutions, for example, a fastening system such as hooks in which the auto-injector is coupled.

As described above, it is important to highlight that the housing 101 may be configured to arrange one or more injector pens. In the case of two or more injector pens, the portable case may comprise a sensor module for each injector pen or a single sensor module for all injector pens. The same may be applied to the control module 104 and the warning module 105.

The main object of the housing 101 is to provide, besides a transport function and a physical, light and thermal protection of the injector pen 106 and the pharmaceutical composition 107 contained in the injector pen, a continuous monitoring of the status of the pharmaceutical composition.

The power module 102 of the electronics comprises an energy source that powers the electronic of the system and saving functions to allow minimal use of and the maximum energy source life. The energy source may be of a single use (e.g. a primary battery or a primary cell) or reusable (e.g. a secondary battery, a solar cell, a micro generator or a network connection). This power module may also comprise a general system switch that allows the complete deactivation of the system. Obviously, this power module may not comprise said general system switch.

The sensor module 103 is arranged in the housing 101 (for example, it may be integrated in the housing) and is configured to provide signals to the control module 104 representing attributes related to the pharmaceutical composition 107 contained in the injector pen 106.

Attributes related to the pharmaceutical composition 107 may be attributes directly related to the pharmaceutical composition or indirectly related to the pharmaceutical composition. Attributes directly related to the pharmaceutical composition may be, for example, characteristics of the pharmaceutical composition (or the pharmaceutical active ingredient comprised in the pharmaceutical composition) such as physicochemical characteristics or temperature. Attributes indirectly related to the pharmaceutical composition may be, for example, the opening of the housing or the emergence of the container device from the housing, which may involve the extraction of the pharmaceutical composition from the housing and consequently the use of the pharmaceutical composition due to, for example, health problems of the user. Another indirect attribute could be the temperature in the vicinity of the container device inside the housing or the temperature of the container device, which may cause the spoilage of the product.

Consequently, in the present examples, the sensor module 103 comprises the following sensor elements:
- at least one sensor element for generating a signal representing a physicochemical characteristic of the pharmaceutical composition 107 contained in the injector pen 106;
- at least one sensor element for measuring the temperature in the vicinity of the injector pen inside the housing 101;
- at least one sensor element for detecting the opening of the housing 101;
- at least one sensor element for detecting the emergence (e.g. the intentional or/and the unintentional emergence) of the injector pen from the housing 101.

At this point it is important to highlight that "at least one sensor for measuring the temperature" may mean at least one sensor for generating a signal representing the temperature.

On the other hand, "at least one sensor element for generating a signal representing a physicochemical characteristic" may mean at least one sensor measuring changes in a physicochemical characteristic and generating a signal representing these changes in the physicochemical characteristic.

Obviously, the sensor module 103 may comprise other sensor elements such as at least one sensor element for measuring the temperature of the injector pen 106, at least one sensor element for measuring the temperature of the pharmaceutical composition 107.

Figures 2A, 2B:
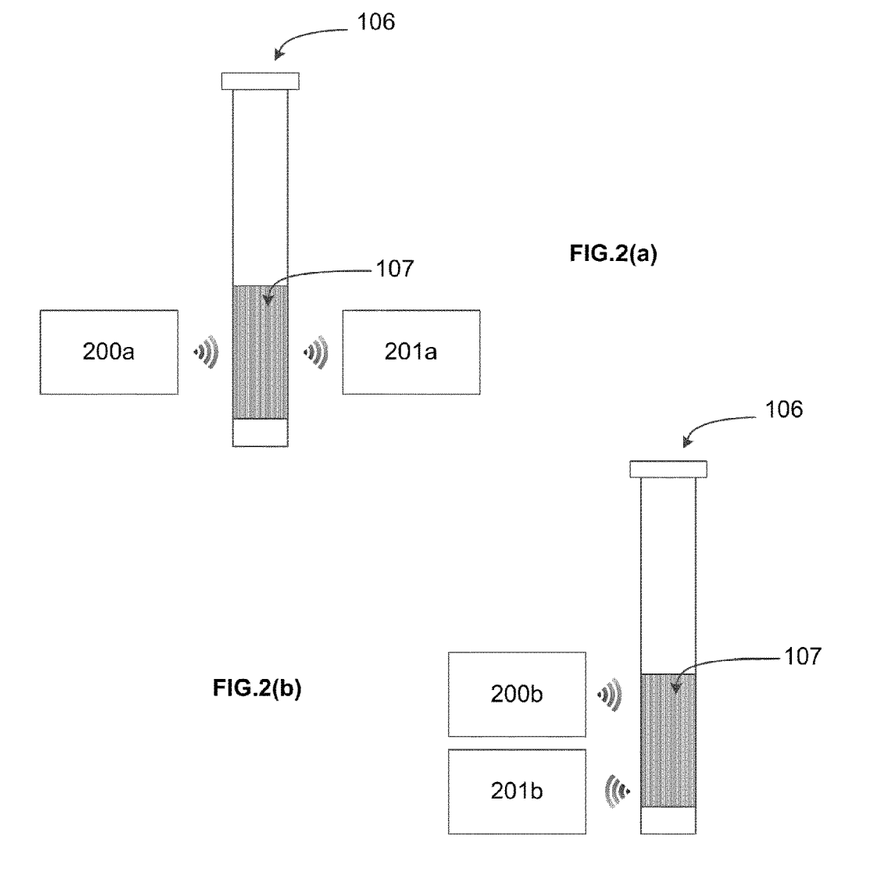
FIGS. 2a, 2b, 2c illustrate block diagrams of different configurations of sensor elements for generating a signal representing a physicochemical characteristic of the pharmaceutical composition.
Figure 2C:
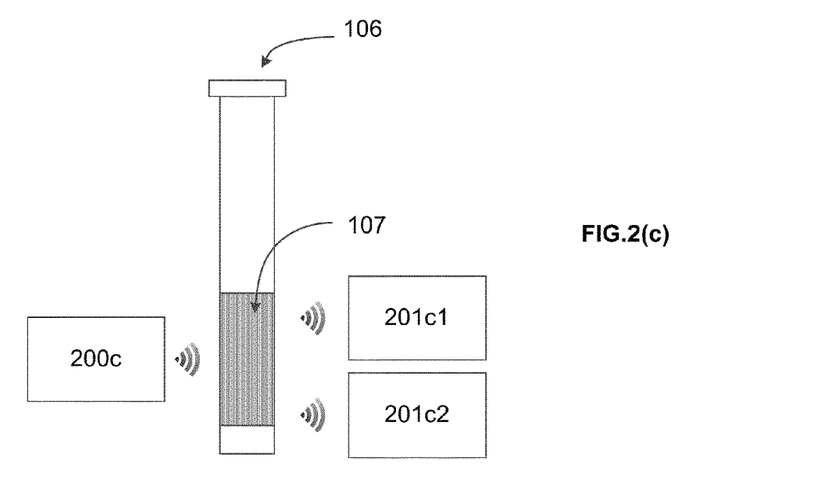

As can be seen in FIG. 2, the at least one sensor element for generating a signal representing a physicochemical characteristic of the pharmaceutical composition 107 may have different configurations (among others).

As shown in FIG. 2(a), the first configuration comprises a transducer 200a configured to generate an electromagnetic signal and a receiver 201a configured to detect changes in the electromagnetic signal generated by the transducer, the transducer and the receiver being arranged opposite to each other. More specifically, the transducer 200a emits an electromagnetic signal (e.g. a light signal), which is detected and measured by the receiver 201a. In its way between the transducer and the receiver, the electromagnetic signal circulates through the injector pen 106 where the pharmaceutical composition 107 to be controlled is contained. The level of, for example, oxidation of the pharmaceutical composition (or of the epinephrine specifically) changes significantly the properties of the electromagnetic signal and these are detected by the receiver 201a (i.e. changes in the oxidation of the epinephrine may cause changes in the physicochemical characteristics of the epinephrine and may involve the spoilage of the epinephrine). This type of electromagnetic signal detection configuration is known as "transmission detection" and it may be suitable when the injector pen 106 comprises two "windows" that allow seeing the pharmaceutical composition 107.

FIG. 2(b) shows a second configuration. This configuration comprises a transducer 200b configured to generate an electromagnetic signal and a receiver 201b configured to detect changes in the electromagnetic signal generated by the transducer, the transducer and the receiver being arranged next to each other. More specifically, FIG. 2(b) shows a configuration where the transducer 200b and the receiver 201b are placed together on the same side of the injector pen 106 containing the pharmaceutical composition 107. In this case the electromagnetic signal or waves emitted by the transducer 200b is directed so that a portion of the emitted waves are transmitted through the pharmaceutical composition while another portion is reflected in the opposite direction of the emitted waves. The reflected waves are altered by the oxidation state of the pharmaceutical composition (or the epinephrine specifically) so that the receiver is able to measure these changes (i.e. changes in the oxidation of the epinephrine may cause changes in the physicochemical characteristics of the epinephrine and may involve the spoilage of the epinephrine). This type of electromagnetic wave detection configuration is known as "reflection detection" and it may be suitable when the injector pen 106 comprises only one "window" that allow seeing the pharmaceutical composition 107.

FIG. 2(c) shows a third configuration. This configuration is a transmission detection structure similar to the first configuration shown in FIG. 2(a). Basically, this configuration comprises a transducer 200c configured to generate an electromagnetic signal and two receivers 201c1, 201c2 configured to be sensitive only in certain frequency bands. The first receiver 201c1 is specifically adjusted to frequency bands absorbed by the pharmaceutical composition (or the epinephrine specifically) when it is in an oxidation state, while the second receiver 201c2 is adjusted to receive any frequency band. The first receiver 201c1 is very sensitive to changes in the state of the pharmaceutical composition (or the epinephrine specifically), while the second receiver 201c2 has a much lower sensitivity to state changes (changes in the oxidation of the epinephrine may cause changes in the physicochemical characteristics of the epinephrine and may involve the spoilage of the epinephrine). This third configuration allows the system to discern the oxidation state of the pharmaceutical composition regardless of the magnitude and intensity of the waves emitted by the transducer 200c. This third configuration may be suitable when the injector pen 106 comprises two "windows" that allow seeing the pharmaceutical composition 107.

In the case of the injector pen 106 comprises only one "window" it is possible to modify said third configuration so that the transducer 200c and the receivers 201c1, 201c2 are placed together on the same side of the injector pen 106.

In any the disclosed configurations, the transducers 200a, 200b, 200c allow converting electrical signals into electromagnetic waves that are directed to the injector pen 106 containing the pharmaceutical composition 107 to be analyzed. The transducer may generate any type of waves according to their frequency and amplitude, such as: sound, radio, light, x-rays, infrared, etc. The transducer receives the signal from the control module 104, which is what decides what time the transducer is put into operation.

On the other hand, the receivers 201a, 201b, 201c1, 201c2 receive the signals emitted by the transducer through the injector pen 106 either transmission or reflection of waves (or other known mechanisms). The receivers are able to distinguish the waves received according to the frequency and to accurately measure their amplitude or intensity. The receiver then sends the data of frequency, amplitude and/or intensity of the received waves to the control module 104 by generating signals representing attributes (in this case, physicochemical characteristics) related to the pharmaceutical composition 107.

At this point, it is important to highlight that any of the three disclosed configurations may be used for injector pens (or any other container device) with its outer surface completely transparent, that is, the pharmaceutical composition is visually accessible from any point of view.

Based on the three disclosed configurations, it is possible to use the technique of visible spectrophotometry. The theoretical definition is the measure of the amount of light absorbed (or any other physicochemical characteristic such as Transmittance, Optical density, Transparency, Attenuation, Diffraction, Fluorescence and/or Refraction) by the pharmaceutical composition analyzed at a certain wavelength. It is based on the emission of light with known characteristics and its analysis by a sensor after passing the substance analyzed. Degradation or changes in the substance are reflected by changes in the light received by the sensor.

Another technique to be used may be the Radiofrequency Spectrometry (RF). This technique is similar to the previous technique but using as a source an emitter of electromagnetic waves in the radio frequency band (from 3 Hz to 300 GHz) and a wave receiver (antenna). Similarly to the previous technique, the passage of electromagnetic waves through the substance allows detecting changes in its properties. This technique may be used when the injector pen 106 does not comprise "windows", that is, the pharmaceutical composition 107 is not visually accessible.

In any case, taking into account the disclosed techniques and configurations (among others), it is possible to obtain at least one physicochemical characteristic of the pharmaceutical composition 107, which allows determining if the pharmaceutical composition is in a suitable or non-suitable status. By way of non-limiting example, the physicochemical characteristics that may be obtained are the following:

Absorbance (the ratio between the amount of radiation of any wavelength that falls into the material (is absorbed), or is refracted or is reflected, to the amount of radiation transmitted through the material, that is, the pharmaceutical composition in the present examples);

Transmittance (the inversely proportional measurement of absorbance of a material);

Optical density (the absorbance of a material when the incident radiation is in the spectrum band of light);

Transparency (the inversely proportional measurement of optical density of a material);

Attenuation (the gradual loss of intensity of radiation of any wavelength when passing through a medium);

Diffraction (the property by which a liquid media with a suspension of solid particles can modify the properties of an incident light source in a way that can be measured by a sensor element);

Fluorescence (the emission of light by a substance that has absorbed light or other electromagnetic radiation);

Refraction (the property of a medium to change the direction of a propagated wave. This change can be specific according to the medium composition, and can be measured numerically using a value called refraction index).

As described above, the sensor module 103 comprises other sensor elements. Thus, the sensor module comprises a set of sensor elements that detect and identify the opening of the housing 101 (e.g. mechanical, magnetic, light, capacitive sensor elements) and the emergence of the injector pen 106 from the housing (or the presence/absence of the injector pen in the housing). For the latter, the presence detection can be carried out using the receiver 201*a*, 201*b*, 201*c*1, 201*c*2 of the configurations previously described.

The warning module 105 comprises all warning mechanisms built into the system itself in response to a warning attribute determined by the control module 104. The warning module comprises physical indicators of different nature, such as light (e.g. incandescent, LED or EL (Electroluminiscence)), sound or haptic (e.g. vibration), which react to events and are controlled by the control module 104.

More specifically, the warning module 105 may comprise, for example, at least one of the following warning elements:

At least one warning element for generating a visual warning;

At least one warning element for generating an audible warning;

At least one warning element for generating a haptic warning.

A warning element for generating a visual warning may be, for example, a display screen (e.g. a LCD display), a plurality of LEDs (Light Emitting Diode), etc. but any other configuration of the warning module is possible.

A warning element for generating an audible warning may be, for example, a speaker, a buzzer, a voice synthesizer, etc.

A warning element for generating a haptic warning may be, for example, any device capable of recreating the sense of touch by applying forces, vibrations, or motions to a user. This way, a vibrator motor may be a warning element for generating a haptic warning.

In the present examples, the warning module 105 may comprise, for example, a set of LEDs, a LCD display, a speaker and a vibrator motor.

The control module 104 receives signals from the sensor module 103, processes it according to a set of programmed control functions and generates trigger signals to be received by the warning module 105.

Thus, the control module 104 is configured to:

Receive at least one signal from the sensor module 104, said signal representing an attribute related to the pharmaceutical composition 107 contained in the injector pen 106;

Determine if the attribute represented by the signal received from the sensor module is a warning attribute;

If the attribute is a warning attribute, generate at least one trigger signal to be received by the warning module 105 configured to generate a warning.

It is important to highlight that the sensor elements may provide the signals to the control module 104 every certain period of time or it may be the control module which causes the sensor elements generating the signals.

The received signal is generated by the following sensor elements comprised in the sensor module 103:

The receiver 201*a*, 201*b*, 201*c*1, 201*c*2 in the case of the physicochemical characteristics of the pharmaceutical composition 107;

The sensor element for measuring the temperature in the vicinity of the injector pen 106 inside the housing 101;

The sensor element for detecting the opening of the housing 101;

The sensor element for detecting the emergence (e.g. the intentional or/and the unintentional emergence) of the injector pen 106 from the housing 101.

For this reason, the control module 104 comprises a set of programmed control functions that may be applied depending on the nature of the received signal.

This way, if the signal received by the control module 104 is a signal representing a physicochemical characteristic of the pharmaceutical composition 107, the control module may determine if the physicochemical characteristic is outside an established range. The definition of said established range basically depends on the physicochemical characteristic, that is, each physicochemical characteristic may require a different range.

Said ranges may be established according to the technical knowledge for each of the physicochemical characteristics. For example, with respect to absorbance, the level of epinephrine oxidation is considered outside the range when the relationship between the absorbance of light in the blue spectrum (470 nm) and the luminous spectrum (380~780 nm) is equal to or greater than 9.

If the value of the physicochemical characteristic represented by the signal provided by the sensor module (i.e. the receiver 201*a*, 201*b*, 201*c*1, 201*c*2) is inside the established range then the physicochemical characteristic of the pharmaceutical composition 107 is acceptable and consequently the status of the product may be suitable for use. On the contrary, if the value of the physicochemical characteristic represented by the signal provided by the sensor module is outside the established range then the physicochemical characteristic of the pharmaceutical composition is not acceptable and consequently the status of the pharmaceutical composition may not be suitable for use or it may be in danger of becoming not suitable for use and a warning indicating this situation may be generated.

In the present examples, depending on the programmed control function, this warning may be generated through the speaker and/or the LCD display and/or the vibrator and/or the set of LEDs.

Thus, the control module 104 may trigger (by means of the generated trigger signal) the speaker to reproduce, for example, by means of voice messages stored in a memory or a voice synthesizer, a message pointing out the change in the physicochemical characteristic of the pharmaceutical composition and that the pharmaceutical composition may be not suitable for use or it is in danger of becoming not suitable for use.

With reference to the LCD display, the control module 104 may trigger the LCD display to show a message pointing out the change in the physicochemical characteristic of the pharmaceutical composition and that the pharmaceutical composition may be not suitable for use or it is in danger of becoming not suitable for use.

In the case of the vibrator, the control module 104 may trigger the vibrator to vibrate in order to suggest the user that there may be a problem in the portable case 100.

On the other hand, the set of LEDs may comprise one LED of orange color, one LED of red color and one LED of green color (obviously, any color is possible and the number of LEDs). This way, it is possible to use different combinations of colors for providing different warnings to the user. Furthermore, it is possible to cause LEDs blink for providing warnings to the user.

In the present examples, the control module 104 may trigger (by means of the trigger signal) the corresponding LED (or a combination of them) to blink. This way, the blinking of the red LED may mean that a physicochemical characteristic is outside its established range; the blinking of the orange LED may mean that the temperature in the vicinity of the injector pen is outside its established range; or the blinking of the green LED may mean that the power module 102 is discharged. Furthermore, the lighting of the orange LED may mean that the housing 101 has been opened and/or the lighting of the red LED may mean that the injector pen 106 has emerged from the housing.

Consequently, if the value of the physicochemical characteristic represented by the signal provided by the sensor module is outside the established range then the control module 104 may trigger the red LED to blink pointing out the change in the physicochemical characteristic of the pharmaceutical composition and that the pharmaceutical composition may be not suitable for use or it is in danger of becoming not suitable for use.

If the signal received by the control module 104 is a signal representing the temperature in the vicinity of the injector pen 106 inside the housing 101, the control module may determine if the temperature is outside an established range. The definition of said established range basically depends on the pharmaceutical composition 107 contained in the injector pen 106. Thus, for example, if the pharmaceutical composition comprises epinephrine said range of temperature may be between 4° C. and 25° C.

If the value of the temperature in the vicinity of the injector pen represented by the signal provided by the sensor module is inside the established range then said temperature is acceptable and consequently the status of the pharmaceutical composition may be suitable for use. On the contrary, if the value of the temperature represented by the signal provided by the sensor module is outside the established range then the value of temperature is not acceptable and consequently the status of the pharmaceutical composition may be not suitable for use or it may be in danger of becoming not suitable for use and a warning indicating this situation may be generated.

Thus, the control module 104 may trigger (by means of the trigger signal) the speaker to reproduce, for example, by means of voice messages stored in a memory or a voice synthesizer, a message pointing out the temperature is outside the established range and that the pharmaceutical composition may be not suitable for use or it is in danger of becoming not suitable for use.

With reference to the LCD display, the control module 104 may trigger the LCD display to show a message pointing out the temperature is outside the established range and that the pharmaceutical composition may be not suitable for use or it is in danger of becoming not suitable for use.

In the case of the vibrator, the control module 104 may trigger the vibrator to vibrate in order to suggest to the user that there may be a problem in the portable case (for example, in the pharmaceutical composition).

With reference to the set of LEDs, the control module 104 may trigger the orange LED to blink pointing out the temperature is outside the established range and that the pharmaceutical composition may be not suitable for use or it is in danger of becoming not suitable for use.

If the signal received by the control module 104 is a signal representing the opening of the housing 101, the control module may determine if the housing has been opened. Basically, if the opening of the housing is detected, a warning may be generated because the user may be, for example, in danger (e.g. the user may have an allergic reaction such as anaphylaxis). On the other hand, said opening of the housing may be due to a visual inspection of the product or a replacement of the container device, for example, because the product has expired. In these cases, a warning may also be generated.

Thus, the control module 104 may trigger (by means of the generated trigger signal) the speaker to reproduce, for example, by means of voice messages stored in a memory or a voice synthesizer, a message pointing out the housing 101 has been opened. Furthermore, the control module may trigger the speaker to reproduce a message pointing out how the injector pen 106 must be used because the opening of the housing may involve the use of the injector pen (the user may be, for example, in danger).

With reference to the LCD display, the control module 104 may trigger the LCD display to show a message pointing out the housing has been opened.

In the case of the vibrator, the control module 104 may trigger the vibrator to vibrate in order to suggest the user that there may be a problem in the portable case.

In the case of the set of LEDs, the control module 104 may trigger the orange LED to turn on pointing out the housing 101 has been opened.

If the signal received by the control module 104 is a signal representing the emergence of the injector pen 106 from the housing 101, the control module may determine if the injector pen has emerged from the housing. Thus, if the emergence of the container device from the housing is detected, a warning may be generated because the user may be, for example, in danger (e.g. the user may have an allergic reaction such as anaphylaxis). On the other hand, said emergence of the container device from the housing may be due to a visual inspection of the product or a replacement of the container device, for example, because the product has expired. In these cases, a warning may also be generated.

This way, the control module 104 may trigger (by means of the trigger signal) the speaker to reproduce, for example, by means of voice messages stored in a memory or a voice synthesizer, a message pointing out the injector pen 106 has emerged from the housing 101. Furthermore, the control module may trigger the speaker to reproduce a message pointing out how the injector pen 106 must be used because the emergence of the injector pen from the housing may involve the use of the injector pen (the user may be, for example, in danger).

With reference to the LCD display, the control module 104 may trigger the LCD display to show a message pointing out the injector pen 106 has emerged from the housing 101.

In the case of the vibrator, the control module 104 may trigger the vibrator to vibrate in order to suggest the user that there may be a problem in the portable case.

In the case of the set of LEDs, the control module 104 may trigger the red LED to turn on, thereby pointing out the injector pen 106 has emerged from the housing 101.

Basically, the control module 104 must be able to reproduce the method described above, for example, by means of electronic and/or computing means. Said electronic/computing means may be used interchangeably, that is, a part of the described means may be electronic means and the other part may be computing means, or all described means may be electronic means or all described means may be computing means. Examples of a control module comprising only electronic means (that is, a purely electronic configuration) may be a programmable electronic device such as a CPLD (Complex Programmable Logic Device), an FPGA (Field Programmable Gate Array) or an ASIC (Application-Specific Integrated Circuit).

An example of a control module comprising only computing means may be a computing device, which may comprise a memory and a processor, the memory being adapted to store a series of computer program instructions, and the processor being adapted to execute these instructions stored in the memory in order to generate the various events and actions for which the control module has been programmed.

On the other hand, the cited computer program may comprise program instructions for causing the control module 104 to perform the method described above according to some examples. The computer program may be embodied on a storage medium (for example, a CD-ROM, a DVD, a USB drive, on a computer memory or on a read-only memory) or carried on a carrier signal (for example, on an electrical or optical carrier signal).

The computer program may be in the form of source code, object code, a code intermediate source and object code such as in partially compiled form, or in any other form suitable for use in the implementation of the method. The carrier may be any entity or device capable of carrying the computer program.

For example, the carrier may comprise a storage medium, such as a ROM, for example a CD ROM or a semiconductor ROM, or a magnetic recording medium, for example a hard disk. Further, the carrier may be a transmissible carrier such as an electrical or optical signal, which may be conveyed via electrical or optical cable or by radio or other means.

When the computer program is embodied in a signal that may be conveyed directly by a cable or other device or means, the carrier may be constituted by such cable or other device or means.

Alternatively, the carrier may be an integrated circuit in which the computer program is embedded, the integrated circuit being adapted for performing, or for use in the performance of, the relevant methods.

According to another examples, the portable case 100 may also comprise a telephone module (not shown), which may be a part of the warning module 105. Said telephone module may be configured to generate external warnings, which may comprise making a telephone call to at least one established telephone number (e.g. the telephone number of any person related to the user or an emergency service). Further or alternatively, if the telephone module comprises mobile data (e.g. mobile Internet data), generating an external warning may also comprise sending an electronic message (for example, an SMS, an email, a Whatsapp or Telegram message, etc.), for example, to the user or to any person related to the user so that said person may know that the user may be in danger. This way, the control module 104 may trigger the telephone module to make a telephone call or to send an electronic message as described.

For improving the operation of the telephone module, the portable case 100 may also comprise a satellite positioning module (not shown). Said module may be used for obtaining the geo-position of the portable case and consequently determining the geo-position of the user in case the user may be in danger (for example, health problems). Said geo-position may be comprised in the external warning generated by the telephone module. This way, it is possible to locate the user. Furthermore, in the case where the user has forgotten the portable case (and consequently the injector pen), he/she will be able to locate it with the geo-positioning.

Figure 3:
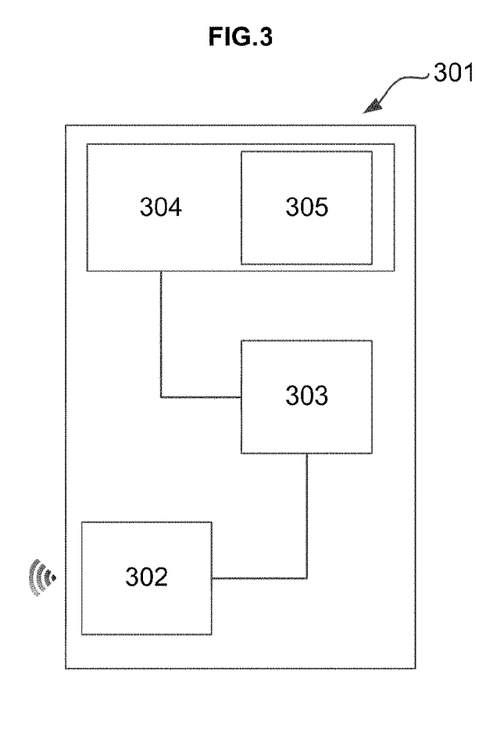
FIG. 3 illustrates a block diagram of a system for controlling a product contained in a container device, said system being connected to an apparatus according to some examples.

According to another examples, as can be seen in FIG. 3, the portable case 100 comprises a communication module 300 configured to communicate the portable case with an apparatus 301, for example a portable apparatus such as a smartphone, a smartwatch, a tablet, etc. In the present examples, the apparatus comprises a smartphone.

As shown in FIG. 3, the smartphone 301 comprises a communication module 302, a control module 303 and a warning module 304.

The communication module 302 of the smartphone 301 is configured to establish a communication with the communication module 300 of the portable case 100. Said smartphone communication module may be of the wired or wireless type. Thus, in the case of being of the wireless type, it might be based on GSM, GPRS, 3G, 4G or satellite technology (e.g. if the communication between the portable case and the smartphone is performed through a global communication network such as the Internet). The wireless communication system might also be short ranged, e.g., of the Bluetooth, NFC, Wifi type, IEEE802.11 or Zigbee.

Said communication between the portable case 100 and the smartphone 301 may be secured by means of, for example, cryptographic keys and/or an SSL tunnel established between them.

In the present examples, the communication module 302 of the smartphone 301 and the communication module 300 of the portable case 100 comprise a wireless communication system and more specifically a Bluetooth system, that is, the portable case and the smartphone are connected via Bluetooth (obviously, the communication module used in the smartphone depends on the communication module used in the portable case). Basically, this established communication between them allows sending data signals and control signals from the control module 104 of the portable case to the control module 303 of the smartphone and vice versa.

If the portable case 100 comprises a set of LEDs in the warning module 105, one LED of the set of LEDs may be, for example, a LED of blue color. Thus, the control module 104 of the portable case may be configured to trigger the blue led to turn on when the Bluetooth communication is established between the portable case and the smartphone. Furthermore, the control module 104 of the portable case may be configured to trigger the blue led to blink when the Bluetooth communication is being established.

The warning module 304 of the smartphone 301 may comprise:
- at least one warning element for generating an audible warning;
- at least one warning element for generating a visual warning; and
- at least one warning element for generating a haptic warning.

In the present examples, because the apparatus is a smartphone, the warning element for generating an audible warning is the smartphone's speaker; the warning element for generating a visual warning is the smartphone's display screen and the warning element for generating a haptic warning is the smartphone's vibrator motor.

The control module 303 of the smartphone 301 (e.g. the processor of the smartphone and other hardware associated with it) is configured to:

Receive at least one trigger signal from the control module 104 of the portable case 100, through the communication established between the communication module 302 of the smartphone and the communication module 300 of the portable case;

Generate at least one warning signal according to the received trigger signal to be received by the warning module 304 of the smartphone configured to generate a warning according to the warning signal.

This way, if the trigger signal received from the control module 104 of the portable case 100 represents that a physicochemical characteristic of the pharmaceutical composition 107 contained in the injector pen 106 is outside an established range, the control module 303 of the smartphone 301 generates a warning signal from which the warning module generates a warning about the physicochemical characteristic being outside the established range.

In the present examples, this warning may be generated by any of the warning elements comprised in the warning module 304 of the smartphone 301, that is, the display screen, the vibrator and/or the speaker of the smartphone.

Thus, the control module 303 of the smartphone 301 may trigger (by means of the generated warning signal) the speaker to reproduce, for example, by means of voice messages stored in a memory or a voice synthesizer, a message pointing out the change in the physicochemical characteristic of the pharmaceutical composition 107 and that the pharmaceutical composition may be not suitable for use or it is in danger of becoming not suitable for use.

With reference to the display screen, the control module 303 of the smartphone 301 may trigger the display screen to show a message pointing out the change in the physicochemical characteristic of the pharmaceutical composition 107 and that the pharmaceutical composition may be not suitable for use or it is in danger of becoming not suitable for use.

In the case of the vibrator, the control module 303 of the smartphone 301 may trigger the vibrator to vibrate in order to suggest the user that there may be a problem in the portable case 100 (for example in the pharmaceutical composition).

According to other examples, as can be seen in FIG. 3, the apparatus may comprise a telephone module 305, which may be a part of the warning module 304. Said telephone module may be configured to generate external warnings, which may comprise making a telephone call to at least one established telephone number (e.g. the telephone number of any person related to the user or an emergency service). Further or alternatively, if the telephone module comprises mobile data (e.g. mobile Internet data), the telephone module 305 may generate external warnings such as electronic messages (for example, an SMS, an email, a Whatsapp or Telegram message, etc.), for example, to the user or to any person related to the user so that said person may know that the user may be in danger.

Because in the present examples the apparatus is a smartphone 301, it comprises its corresponding telephone module 305.

Consequently, in the present examples, the control module 303 of the smartphone 301 may trigger the telephone module 305 to make a telephone call or send an electronic message to the user or to any person related to the user (e.g. if the user is a child or a teenager, said telephone call or said electronic message may be made or sent respectively to his/her parents) pointing out the change in the physicochemical characteristic of the pharmaceutical composition 107 and that the pharmaceutical composition may be not suitable for use or it is in danger of becoming not suitable for use. In the case of a telephone call, the message may be provided, for example, by means of an audio message stored in a memory of the smartphone 301 or by means of a voice synthesizer. On the contrary, in the case of an electronic message, the content of the electronic message may be stored in a memory of the smartphone.

If the trigger signal received from the control module 104 of the portable case 100 represents that the temperature in the vicinity of the injector pen 106 inside the housing is outside an established range, the control module 303 of the smartphone 301 generates a warning signal from which the warning module 304 generates a warning about the temperature in the vicinity of the injector pen inside the housing being outside the established range.

Thus, the control module 303 of the smartphone 301 may trigger (by means of the warning signal) the speaker to reproduce a message pointing out the temperature in the vicinity of the injector pen 106 inside the housing is outside the established range and that the pharmaceutical composition 107 may be not suitable for use or it is in danger of becoming not suitable for use.

With reference to the display screen, the control module 303 of the smartphone 301 may trigger the display screen to show a message pointing out the temperature in the vicinity of the injector pen 106 inside the housing is outside the established range and that the pharmaceutical composition 107 may be not suitable for use or it is in danger of becoming not suitable for use.

In the case of the vibrator, the control module 303 of the smartphone 301 may trigger the vibrator to vibrate in order to suggest the user that there may be a problem in the portable case 100 (for example in the pharmaceutical composition 107).

On the other hand, the control module 303 of the smartphone 301 may trigger the telephone module 305 to make a telephone call or send an electronic message to any person related to the user (e.g. if the user is a child or a teenager, said telephone call or said electronic message may be made or sent respectively to his/her parents) pointing out the temperature in the vicinity of the injector pen 106 inside the housing is outside the established range and that the pharmaceutical composition 107 may be not suitable for use or it is in danger of becoming not suitable for use. In the case of a telephone call, the message may be provided, for example, by means of an audio message stored in a memory of the smartphone or by means of a voice synthesizer. On the contrary, in the case of an electronic message, the content of the electronic message may be stored in a memory of the smartphone.

If the trigger signal received from the control module 104 of the portable case 100 represents the opening of the housing 101, the control module 303 of the smartphone 301 generates a warning signal from which the warning module generates a warning asking to the user the reason for the opening of the housing.

Thus, the control module 303 of the smartphone 301 may trigger (by means of the generated warning signal) the speaker to reproduce a message asking the reason for the opening of the housing 101. Furthermore, the speaker may provide a solution to the user for answering the question. This way, for example, the user may provide the reason through the microphone of the smartphone. Alternatively or additionally the control module of the smartphone may trigger the display screen to show buttons or similar, one for each possible reason. Consequently, the user may select the reason and generate a response pressing the corresponding button. Basically, the reason provided by the user may relate to a replacement of the injector pen 106, a visual inspection of the product or the use of the injector pen.

With reference to the display screen, the control module 303 of the smartphone 301 may trigger the display screen to show a message asking the reason for the opening of the housing 101. Furthermore, the display screen may show buttons or similar, one for each possible reason.

In the case of the vibrator, the control module 303 of the smartphone 301 may trigger the vibrator to vibrate in order to suggest the user that there may be a problem in the portable case 100 (for example in the pharmaceutical composition).

On the other hand, the control module 303 of the smartphone 301 may trigger the telephone module 305 to make a telephone call or send an electronic message to any person related to the user (e.g. if the user is a child or a teenager, said telephone call or said electronic message may be made or sent respectively to his/her parents) asking the reason for the opening of the housing 101. In the case of a telephone call, the message may be provided, for example, by means of an audio message stored in a memory of the smartphone or by means of a voice synthesizer (the audio message may provide a solution to the user for answering the question as described for the speaker). On the contrary, in the case of an electronic message, the content of the electronic message may be stored in a memory of the smartphone. Said content of the electronic message may comprise a solution for answering the question, for example, providing one link for each possible reason.

If the trigger signal received from the control module 104 of the portable case 100 represents the emergence of the injector pen 106 from the housing 101, the control module 303 of the smartphone 301 generates a warning signal from which the warning module generates a warning asking the reason for the emergence of the injector pen from the housing.

Thus, the control module 303 of the smartphone 301 may trigger (by means of the warning signal) the speaker to reproduce a message asking the reason for the emergence of the injector pen 106 from the housing 101. Furthermore, the speaker may provide a solution to the user for answering the question. This way, for example, the user may provide the reason through the microphone of the smartphone. Alternatively or additionally the control module of the smartphone may trigger the display screen to show buttons or similar, one for each possible reason. Basically, the reason provided by the user may relate to a replacement of the injector pen 106, a visual inspection of the product (i.e. the pharmaceutical composition) or the use of the injector pen.

With reference to the display screen, the control module 303 of the smartphone 301 may trigger the display screen to show a message asking the reason for the emergence of the injector pen 106 from the housing 101. Furthermore, the display screen may show buttons or similar, one for each possible reason.

In the case of the vibrator, the control module 303 of the smartphone 301 may trigger the vibrator to vibrate in order to suggest to the user that there may be a problem in the portable case 100 (for example in the pharmaceutical composition).

On the other hand, the control module 303 of the smartphone 301 may trigger the telephone module 305 to make a telephone call or send an electronic message to any person related to the user (e.g. if the user is a child, said telephone call or said electronic message may be made or sent respectively to his/her parents) asking the reason for the emergence of the injector pen 106 from the housing 101. In the case of a telephone call, the message may be provided, for example, by means of an audio message stored in a memory of the smartphone or by means of a voice synthesizer (the audio message may provide a solution to the user for answering the question as described for the speaker). On the contrary, in the case of an electronic message, the content of the electronic message may be stored in a memory of the smartphone. Said content of the electronic message may comprise a solution for answering the question, for example, providing one link for each possible reason.

In both cases (the opening of the housing and the emergence of the injector pen from the housing), the control module 303 of the smartphone 301 waits for receiving a response to the warning within an established time period.

If a response is not received (it may mean that the user may be in danger, for example, with a health problem), the control module 303 of the smartphone 301 generates an external warning, for example, to any person related to the user or to any emergency service.

If the smartphone 301 comprises a satellite positioning system (e.g. a GPS), the control module 303 of the smartphone may obtain the geo-position of the smartphone (that is the same as the user) and the external warning may comprise said geo-position. This way, the user may be located easily.

Basically, the disclosed external warning only may be generated by the telephone module 305, because the warning (i.e. the external warning) should not be received by the user but, for example, for any person related to him/her or for an emergency service.

For this reason, the control module 303 of the smartphone 301 may trigger the telephone module 305 to make a telephone call or send an electronic message to any person related to the user or to an emergency service pointing out that the user may be in danger. In the case of a telephone call, the message may be provided, for example, by means of an audio message stored in a memory of the smartphone or by means of a voice synthesizer. On the contrary, in the case of an electronic message, the content of the electronic message may be stored in a memory of the smartphone.

If a response is received by the control module 303 of the smartphone 301, said control module determines a reason for the opening of the housing or for the emergence of the injector pen 106 from the housing taking into account the received response. If the reason relates to a replacement of the injector pen 106, the control module of the smartphone generates a warning signal from which the warning module 304 of the smartphone generates a warning comprising instructions about the replacement of the injector pen.

Thus, the control module 303 of the smartphone 301 may trigger (by means of the warning signal) the speaker to reproduce a message comprising instructions about the replacement of the injector pen 106. Said instructions, for example, may be stored in a memory of the smartphone.

With reference to the display screen, the control module 303 of the smartphone 301 may trigger the display screen to show a video comprising instructions about the replacement of the injector pen 106.

On the other hand, the control module 303 of the smartphone 301 may trigger the telephone module 305 to make a telephone call or send an electronic message to any person related to the user pointing out the injector pen has been replaced. In the case of a telephone call, the message may be provided, for example, by means of an audio message stored in a memory of the smartphone or by means of a voice synthesizer. On the contrary, in the case of an electronic message, the content of the electronic message may be stored in a memory of the smartphone.

If the reason for the opening of the housing 101 or for the emergence of the injector pen 106 from the housing relates to the use of the injector pen, the control module 303 of the smartphone 301 generates a warning signal from which the warning module generates a warning comprising instructions about the use of the injector pen.

Thus, the control module 303 of the smartphone 301 may trigger (by means of the warning signal) the speaker to reproduce a message comprising instructions about the use of the injector pen. Said instructions, for example, may be stored in a memory of the smartphone and may be useful for the user or for any person nearby to the user that may be helping him/her.

With reference to the display screen, the control module 303 of the smartphone 301 may trigger the display screen to show a video comprising instructions about the use of the injector pen 106. Said video, for example, may be stored in a memory of the smartphone (or may be received by the smartphone in streaming through the corresponding mobile Internet data of the telephone module 305) and again may be useful for the user or for any person nearby to the user that may be helping him/her.

On the other hand, the control module 303 of the smartphone 301 may trigger the telephone module 305 to make a telephone call or send an electronic message (that is, the control module generates an external warning) to any person related to the user pointing out the injector pen has been used. In the case of a telephone call, the message may be provided, for example, by means of an audio message stored in a memory of the smartphone or by means of a voice synthesizer. On the contrary, in the case of an electronic message, the content of the electronic message may be stored in a memory of the smartphone.

If the smartphone 301 comprises a satellite positioning module (e.g. a GPS), the control module 303 of the smartphone may obtain the geo-position of the smartphone (which is the same as the user) and the external warning described above may comprise said obtained geo-position. This way, the user may be located easily.

Obviously, it is very important to control if the communication between the portable case 100 and the smartphone 301 is established or not. For this reason, the control module 303 of the smartphone, randomly or at certain time, determines if a communication is established between the communication module 302 of the smartphone and the communication module 300 of the portable case. In case the communication is not established, the control module of the smartphone generates a warning signal from which the warning module generates a warning about no communication established between the smartphone and the portable case.

Thus, the control module 303 of the smartphone 301 may trigger (by means of the warning signal) the speaker to reproduce a message pointing out a communication is not established between the smartphone and the portable case. Said message, for example, may be stored in a memory of the smartphone.

With reference to the display screen, the control module 303 of the smartphone 301 may trigger the display screen to show a message pointing out a communication is not established between the smartphone and the portable case 100.

On the other hand, the control module 303 of the smartphone 301 may trigger the telephone module 305 to make a telephone call or send an electronic message to the user (for example, an email) or to any person related to the user pointing out a communication is not established between the smartphone and the portable case 100. In the case of a telephone call, the message may be provided, for example, by means of an audio message stored in a memory of the smartphone or by means of a voice synthesizer. On the contrary, in the case of an electronic message, the content of the electronic message may be stored in a memory of the smartphone.

Basically, the control module 303 of the smartphone 301 must be able to reproduce the method described above, for example, by means of electronic and/or computing means. Said electronic/computing means may be used interchangeably, that is, a part of the described means may be electronic means and the other part may be computing means, or all described means may be electronic means or all described means may be computing means. Examples of a control module 303 comprising only electronic means (that is, a purely electronic configuration) may be a programmable electronic device such as a CPLD, an FPGA or an ASIC.

An example of a control module 303 comprising only computing means may be a computing device, which may comprise a memory and a processor, the memory being adapted to store a series of computer program instructions, and the processor being adapted to execute these instructions stored in the memory in order to generate the various events and actions for which the control module has been programmed.

On the other hand, the cited computer program may comprise program instructions for causing the control module 303 to perform the method described above according to some examples. The computer program may be embodied on a storage medium (for example, a CD-ROM, a DVD, a USB drive, on a computer memory or on a read-only memory) or carried on a carrier signal (for example, on an electrical or optical carrier signal).

The computer program may be in the form of source code, object code, a code intermediate source and object code such as in partially compiled form, or in any other form suitable for use in the implementation of the method. The carrier may be any entity or device capable of carrying the computer program.

For example, the carrier may comprise a storage medium, such as a ROM, for example a CD ROM or a semiconductor ROM, or a magnetic recording medium, for example a hard disk. Further, the carrier may be a transmissible carrier such as an electrical or optical signal, which may be conveyed via electrical or optical cable or by radio or other means.

When the computer program is embodied in a signal that may be conveyed directly by a cable or other device or means, the carrier may be constituted by such cable or other device or means.

Alternatively, the carrier may be an integrated circuit in which the computer program is embedded, the integrated circuit being adapted for performing, or for use in the performance of, the relevant methods.

Although only a number of particular embodiments and examples of the invention have been disclosed herein, it will be understood by those skilled in the art that other alternative embodiments and/or uses of the invention and obvious modifications and equivalents thereof are possible. Furthermore, the present invention covers all possible combinations of the particular embodiments described. Thus, the scope of the present invention should not be limited by particular embodiments, but should be determined only by a fair reading of the claims that follow.

The invention claimed is:

1. A method of controlling a product contained in a container device such that it is detected whether the product contained in the container device is in a suitable status to be used, the product being a drug, the container device being a drug delivery device, the method comprising, when the drug delivery device is arranged in a housing:
   receiving at least one signal from a sensor module, the signal representing an attribute related to the drug contained in the drug delivery device, the sensor module being associated with the housing;
   determining if the attribute represented by the signal received from the sensor module is a warning attribute; and
   if the attribute is a warning attribute, generating at least one trigger signal to be received by at least a warning module configured to generate a warning based on the trigger signal,
   wherein the received signal representing the attribute comprises a signal representing a physiochemical characteristic of the drug,
   the determining if the attribute representing by the signal received from the sensor module is a warning attribute comprises determining if the physicochemical characteristic of the drug contained in the drug delivery device is outside an established range, and
   if a value of the physicochemical characteristic represented by the signal provided by the sensor module is outside the established range, determining that the status of the drug is not suitable for use.

2. The method according to claim 1, wherein the physicochemical characteristic comprises at least one of the following physiochemical characteristics:
   absorbance;
   transmittance;
   optical density;
   transparency;
   attenuation;
   diffraction;
   fluorescence; and
   refraction.

3. The method according to claim 1, wherein the received signal representing the attribute comprises a signal representing a temperature in the vicinity of the drug delivery device and inside the housing, and wherein:
   determining if the attribute represented by the signal received from the sensor module is a warning attribute comprises determining if the temperature in the vicinity of the drug delivery device inside the housing is outside an established range.

4. The method according to claim 1, wherein the received signal representing the attribute comprises a signal representing a temperature of the drug delivery device, and wherein:
   determining if the attribute represented by the signal received from the sensor module is a warning attribute comprises determining if the temperature of the drug delivery device is outside an established range.

5. The method according to claim 1, wherein the received signal representing the attribute comprises a signal representing a temperature of the drug, and wherein:
   determining if the attribute represented by the signal received from the sensor module is a warning attribute comprises determining if the temperature of the drug is outside an established range.

6. The method according to claim 1, wherein the received signal representing the attribute comprises a signal representing an opening of the housing, and wherein:
   determining if the attribute represented by the signal received from the sensor module is a warning attribute comprises determining if the housing has been opened.

7. The method according to claim 1, wherein the received signal representing the attribute comprises a signal representing the emergence of the drug delivery device from the housing, and wherein:
   determining if the attribute represented by the signal received from the sensor module is a warning attribute comprises determining if the drug delivery device has emerged from the housing.

8. A control module comprising a memory and a processor, embodying instructions stored in the memory and executable by the processor, the instructions comprising functionality to execute the method according to claim 1.

9. A control module for controlling a drug contained in a drug delivery device, when the drug delivery device is arranged in a housing, the control module comprising:
   means for receiving at least one signal from a sensor module, the signal representing an attribute related to the drug contained in the drug delivery device, the sensor module being associated with the housing;
   means for determining if the attribute represented by the signal received from the sensor module is a warning attribute; and
   means for generating, if the attribute is a warning attribute, at least one trigger signal to be received by at least a warning module configured to generate a warning based on the trigger signal,
   wherein
   the signal representing the attribute comprises a signal representing a physiochemical characteristic of the drug,
   the determining if the attribute representing by the signal received from the sensor module is a warning attribute comprises determining if the physicochemical characteristic of the drug contained in the drug delivery device is outside an established range, and
   if a value of the physicochemical characteristic represented by the signal provided by the sensor module is outside the established range, the warning indicates that the status of the drug is not suitable for use.

10. A system comprising:
    a housing configured for at least one drug delivery device arranged therein;
    at least one sensor module configured to generate at least one signal representing an attribute related to a drug contained in the drug delivery device, the sensor module being associated with the housing;
    at least one control module according to claim 9, the control module being associated with the housing; and
    at least one warning module configured to generate a warning based on the trigger signal generated by the control module.

11. The system according to claim 10, wherein the sensor module comprises at least one sensor element for generating a signal representing a physicochemical characteristic of the drug.

12. The system according to claim 11, wherein the at least one sensor element for generating a signal representing a physicochemical characteristic of the drug comprises at least one transducer configured to generate a signal and at least one receiver configured to detect changes in the signal generated by the at least one transducer.

13. The system according to claim 12, wherein the at least one transducer and the at least one receiver are arranged next to each other or are arranged opposite to each other.

14. The system according to claim 10, further comprising a communication module for communications from the system to an apparatus.

15. A method of generating warning signals in an apparatus, the apparatus comprising a control module, a communication module and a warning module, the method comprising:

the apparatus control module receiving at least one trigger signal from a control module of the system according to claim 14 for controlling a drug contained in a drug delivery device, through a communication established between the apparatus communication module and the system communication module; and the apparatus control module generating at least one warning signal according to the received trigger signal to be received by the apparatus warning module configured to generate a warning according to the warning signal.

16. The method according to claim 15, wherein the trigger signal received from the system control module represents that a physicochemical characteristic of the drug contained in the drug delivery device is outside an established range, and wherein:

generating a warning signal comprises generating a warning signal from which the warning module generates a warning about the physicochemical characteristic being outside the established range.

17. The method according to claim 15, wherein the trigger signal received from the system control module represents that the temperature in the vicinity of the drug delivery device inside the housing is outside an established range, and wherein:

generating a warning signal comprises generating a warning signal from which the warning module generates a warning about the temperature in the vicinity of the drug delivery device inside the housing being outside the established range.

* * * * *